United States Patent [19]

Wang

[11] Patent Number: 5,796,105
[45] Date of Patent: Aug. 18, 1998

[54] EXTENDED RANGE OPTICAL SCINTILLOMETER WITH INTERRUPTION PROTECTION FOR MEASURING ATMOSPHERIC REFRACTIVE TURBULENCE

[76] Inventor: Ting-I Wang, 205 Perry Pkwy., Suite 14, Gaithersburg, Md. 20877

[21] Appl. No.: 709,159

[22] Filed: Sep. 6, 1996

Related U.S. Application Data

[60] Provisional application No. 60/003,459, Sep. 8, 1995.
[51] Int. Cl.$^6$ ................................................ G01N 21/41
[52] U.S. Cl. .................................................. 250/338.5
[58] Field of Search ........................... 250/338.1, 338.5; 356/128

[56] References Cited

U.S. PATENT DOCUMENTS

| | | |
|---|---|---|
| 4,760,272 | 7/1988 | Wang . |
| 4,937,447 | 6/1990 | Barrett .................. 250/338.5 X |
| 5,150,171 | 9/1992 | Hill et al. ..................... 356/128 |
| 5,303,024 | 4/1994 | Thierman ..................... 356/128 |
| 5,444,530 | 8/1995 | Wang . |
| 5,528,224 | 6/1996 | Wang . |

OTHER PUBLICATIONS

Winstanley et al., "Point Visibility Meter: A forward scatter instrument for the measurement of aerosol extinction coefficient", Applied Optics, vol. 14, No. 9, Sep. 1975, pp. 2151–2157.

Kazovsky, "An Optical Rain Gauge Based on Forward Scattering", IEEE Transaction on Geoscience and Remote Sensing, vol. GE–23, No. 2, Mar. 1985, pp. 124–131.

Earnshaw et al., "A Feasability Study of Indentifying Weather by Laser Forward Scattering", Journal of Applied Meteorology, vol. 17, Oct. 1978, pp. 1478–1481.

Wang et al., "Laser Weather Identifier: Present and Future", Journal of Applied Meteorology, vol. 21, No. 11, Nov. 1982, pp. 1747–1753.

HHS, Inc. HHS–TD–083 Jun. 1982 VR–301 Visibility Meter, Technical Data Sheets, 19 pages.

*Primary Examiner*—Edward J. Glick
*Attorney, Agent, or Firm*—Charles H. Thomas

[57] ABSTRACT

An optical scintillometer is provided which is operative to measure atmospheric turbulence intensity up to a distance of two and a half kilometers. The optical scintillometer provides real time continuous measurements of turbulence intensity in the field of operations employing a transmitter, receiver, and digital processing circuitry. The signal is digitized before comparison with a threshold to eliminate events attributable to objects moving through the path of the optical transmitter and receiver. The system is thereby able to perform calculations to adjust the first order log-amplitude variance function in the saturation regime. An extremely important aspect of the invention is the digitization of the signal and its comparison with the threshold signal. Because a digital signal is compared with a threshold signal level, invalid signal inputs are excluded from the calculation of path-averaged turbulence intensity. The exclusion of such signals assures the data quality in computing the refractive turbulence intensity even when there is an interruption of the infrared beam. This feature is critical for the data processing. Data produced when the optical path is obstructed by moving vehicles, pedestrians, and airplanes is not used for processing to protect the quality of the output measurements.

16 Claims, 10 Drawing Sheets

EXTENDED RANGE OPTICAL SCINTILLOMETER WITH INTERRUPTION PROTECTION FOR MEASURING ATMOSPHERIC REFRACTIVE TURBULENCE

BACKGROUND OF THE INVENTION

This application claims the benefit of U.S. Provisional Application 60/003,459, filed Sep. 8, 1995.

1. Field of the Invention

The present invention relates to a system for accurately measuring intensity of atmospheric turbulence at ground level in turbulent air conditions.

2. Description of the Prior Art

Atmospheric, turbulence-induced optical scintillations have long been a problem in astronomical observation. However, it is also known that observations of the twinkling of stars and the motion of satellite images yield information about the turbulence and the wind speed in the upper atmosphere.

It is known that the path-averaged refractive turbulence structure constant ($C_n^2$) in the weak-scattering region can be measured by the log-irradiance (or log-amplitude) scintillation of an optical wave propagated through the atmosphere. Prior optical scintillometers are based on the first-order scattering theory, and are reliable only as long as the integrated amount of refractive turbulence is small. As the strength of refractive turbulence increases, the scintillations saturate and any scintillometer whose performance is based on the proportionality of log-amplitude variance and refractive turbulence will fail.

SUMMARY OF THE INVENTION

According to the present invention, a diagnostic technique and apparatus has been devised which measures path-averaged atmospheric turbulence intensity along a horizontal path. It is known that a scintillometer with an optical aperture of 0.15 meter was designed to operate up to a distance of 1 kilometer according to the first-order theory. However, with the help of a theory developed to allow measurement of atmospheric turbulence in the saturation regime, according to the present invention, a second generation optical scintillometer with the same optics is able to measure atmospheric turbulence intensity up to a distance of 2.5 kilometers.

The instrument of the present invention provides real-time continuous measurements of turbulence intensity in the field operation. An extremely important aspect of the invention is that the present invention has interruption protection. When the optical path is obstructed by moving vehicles, pedestrians, airplanes, and the like, the invalid data will not be used for processing to protect the quality of the output measurements. Earlier analog systems required several minutes to recover from a visually obscuring obstruction in the path. The new invention with digital processing needs only a few seconds after the interruption for recovery. Therefore, the scintillometer can be installed across a highway, a runway, or a hallway without jeopardizing the performance of the instrument. The instrument is insensitive to environmental acoustic and electromagnetic noises. It is also compact for easy transportation and operation.

According to the present invention, formulas have now been derived that describe the performance of an optical refractive turbulence sensor in strong turbulence. Based on this theory, a turbulence sensor that maintains its calibration in both weak and strong turbulence conditions has now been designed and tested.

Table A shows the required transmitter and receiver optics diameter as a function of path length for measurement without saturation. Table A gives the longest effective path length without saturation effect for a given optical aperture diameter D (for $C_n^2 = 10^{-12}$ m$^{-2/3}$).

TABLE A

| D | L |
|---|---|
| 177 mm (7 in.) | 1 km |
| 536 mm (21 in.) | 2 km |
| 1027 mm (40 in.) | 3 km |

Table A indicates that a scintillometer using 6-inch (152 millimeters) apertures on both transmitter and receiver optics will have an effective path length of less than 1 kilometer (for $C_n^2 = 10^{-12}$ m$^{-2/3}$). To extend the range to 2 kilometers, 21-inch (536 millimeter) and to 3 kilometers, 40-inch (1027 millimeters) optics need to be used to avoid a saturation effect on atmospheric turbulence-induced optical scintillation. However, it is impractical to design such a large aperture optical system for field operation. However, using the system of the present invention, the effective path length of a finite aperture system can be extended for operating even in the saturation regime.

According to the present invention the saturation effects of the turbulence-induced optical scintillation of a finite aperture system have been analyzed to measure path-averaged refractive turbulence along a line-of-sight path. The analytic results show that path-averaged refractive turbulence can be accurately measured even in the saturation region provided that proper corrections are applied to the measured log-amplitude variance of the optical scintillations. The results indicate that it is feasible to design a finite aperture system to measure path-averaged refractive turbulence up to a distance of 2.5 kilometers using 6-inch (152 millimeters) transmitting and receiving apertures.

The saturation effect of the log-amplitude variance is that the measured variance deviates away from the first-order theoretical predictions as turbulence increases. However, in a slight saturation regime, the measured variances are still useful to obtain the path-averaged turbulence intensities if a correction is applied based on the saturation curve of a finite aperture system.

The correction of first order log-amplitude variants involves a number of parameters which are as defined below.

$\sigma_x^2$ = log-amplitude variance u = normalized path length

W(u) = path weighting function (i.e., what is the contribution at different positions of paths)

y = normalized wave number of atmospheric turbulence dy = normalized wave number differential increment g = defined in Equation (3)

$\sigma_T^2$ = theoretical prediction of wake scattering k = wave number of optical source L = path length $C_n^2$ = atmospheric turbulence refractive structure constant $\alpha_t$ = diameter of transmitter normalized to Fresnel size $\alpha_r$ = diameter of receiver normalized to Fresnel size $\sigma_D^2$ = log-amplitude variance of finite transmitter and receiver with aperture D in weak turbulence region $f_c$ = center frequency of band pass filter $J_1$ = first order Bessel function of the first kind Based on earlier analysis, the first order log-amplitude variance function is given by $$\sigma_x^2 = \int_0^1 du C_n^2(u) W(u) \tag{1}$$

where $$W(u) = 0.365 \, k^{7/6} L^{11/6} |u(1-u)|^{5/6} \int_0^\infty dy g(u,y) \tag{2}$$

$$g(u,y) = y^{-11/6} \sin^2 y \exp\{-\sigma_T^2 |u(1-u)|^{5/6} F(y)\} \times \left(\frac{2J_1\{|\pi y u/(1-u)|^{1/2} \alpha_r\}}{|\pi y u/(1-u)|^{1/2} \alpha_r}\right)^2 \left(\frac{2J_1\{|\pi y(1-u)/u|^{1/2} \alpha_t\}}{|\pi y(1-u)/u|^{1/2} \alpha_t}\right)^2, \tag{3}$$

and $$F(y) \simeq \begin{cases} 7.9 y^{5/6} & \text{if } y \leq 1 \\ 7.9 y^{-5/6} & \text{if } y \geq 1 \end{cases} \tag{4}$$

The saturation region may be defined as the region of strong turbulence. In strong turbulence the difference between the first order log-amplitude variance and the corrected log-amplitude variance is the exponential term in Equation (3).

In Equations (2)–(4), $$\sigma_T^2 = 0.124 k^{7/6} L^{11/6} C_n^2 \tag{5}$$

is the weak scattering predicted log-amplitude variance for a point source and receiver. $\alpha_r$ and $\alpha_t$ are, respectfully, the diameters of the receiver and transmitter normalized to a Fresnel zone for the optical path, and $J_1$ is the first-order Bessel function of the first kind. Equation (3) differs from the first-order scattering theory by only the exponential term. For weak turbulence ($\sigma_T^2 \ll 1$), consequently, this term can be neglected. While a precise demarcation between weak turbulence and the saturation regime can be somewhat subjective for purposes of the present invention, strong turbulence or the saturation regime may be considered to be the condition at which $\sigma_T^2$ is greater than 0.3.

In one broad aspect the present invention may be considered to be a method of determining temporally and spatially averaged atmospheric turbulence comprising: generating an infrared optical signal; collimating the infrared optical signal utilizing an optical collimator no greater than about 0.25 meters in size; transmitting the collimated optical signal through atmosphere over a distance greater than one kilometer; receiving the transmitted optical signal and focusing the transmitted optical signal onto a photodetector utilizing a focusing device no greater than about 0.25 meters in size, thereby generating received analog signals; converting the received analog signals to digital form to produce received digital signals; comparing each of the received digital signals with a predetermined digital threshold level to produce data output signals for only those of the received digital signals that are at least as great as the predetermined digital threshold level, and calculating the path averaged log amplitude variance of the data output signals to provide an atmospheric turbulence refractive structure constant. The necessary conversion and calculation is achieved by first digitally correcting the data signals for saturation effect on atmospheric turbulence induced optical scintillation.

In the preferred practice of the method the optical signal is collimated utilizing an optical collimator no greater than about 0.15 meters in size and focused utilizing a focusing device no greater than about 0.15 meters in size. The collimated optical signals are preferably transmitted through atmosphere over a distance greater than two kilometers.

In another broad aspect the invention may be considered to be an optical scintillometer that provides an output corrected for air turbulence comprising: an optical transmitter assembly including an infrared light source and an optical collimating means no greater than about 0.25 meters in size; an optical receiver assembly located from the optical transmitter assembly a distance greater than one kilometer and including an optical focusing means no greater than about 0.25 meters in size and an infrared photodetector that produces a received signal; and signal processing means for producing an atmospheric turbulence refractive structure constant compensated for refractive turbulence including analog to digital conversion means for converting the received signal from analog to digitized form, comparator means for comparing the digitized received signal with a predetermined digital threshold level and producing data outputs therefrom only when the digitized received signal is at least as great as the threshold signal, and root mean square determination and signal averaging means coupled to the comparator means to receive outputs therefrom which are processed to provide the atmospheric turbulence refractive structure constant.

An optical scintillometer according to the invention preferably is comprised of digital saturation effect compensation means for correcting the data output for saturation effects due to atmospheric turbulence. This digital saturation effect compensation means corrects the data outputs for variances from first order log amplitude measurement of scintillation intensity due to refractive turbulence. That is the digital saturation effect compensation means corrects the data outputs for variance of refractive turbulence from proportionality to log amplitude of scintillation measurements.

In an optical scintillometer according to the invention the optical collimating means and the optical focusing means are both normally formed of concave mirrors each having a diameter no greater than about 0.25 meters. Each is preferably no greater than about 0.15 meters in diameter. The optical transmitter assembly and the optical receiver assembly are preferably located from each other a distance of at least two kilometers.

In still another broad aspect the invention may be considered to be an improvement in a scintillometer for measuring path averaged atmospheric turbulence intensity along a path between an optical transmitter and an optical receiver providing analog data outputs and employing a signal processor that includes root mean square and averaging circuity to provide an atmospheric turbulence refractive structure constant. The improvement is comprised of an analog to digital converter that digitizes the analog data outputs from the receiver and digital saturation effect compensation means that corrects the data outputs from the receiver in their digital form for variances from first order log amplitude measurement of scintillation intensity due to refractive turbulence. The comparator means compares signals from the receiver in their digital form with a predetermined threshold level and provides data outputs to the root mean square and averaging circuitry only in response to signals from the receiver in their digital form that are at least as great as the digital threshold level.

The invention may be described with greater clarity and particularity by reference to the accompanying drawings.

DESCRIPTION OF THE METHOD AND THE EMBODIMENT

Figure 1:
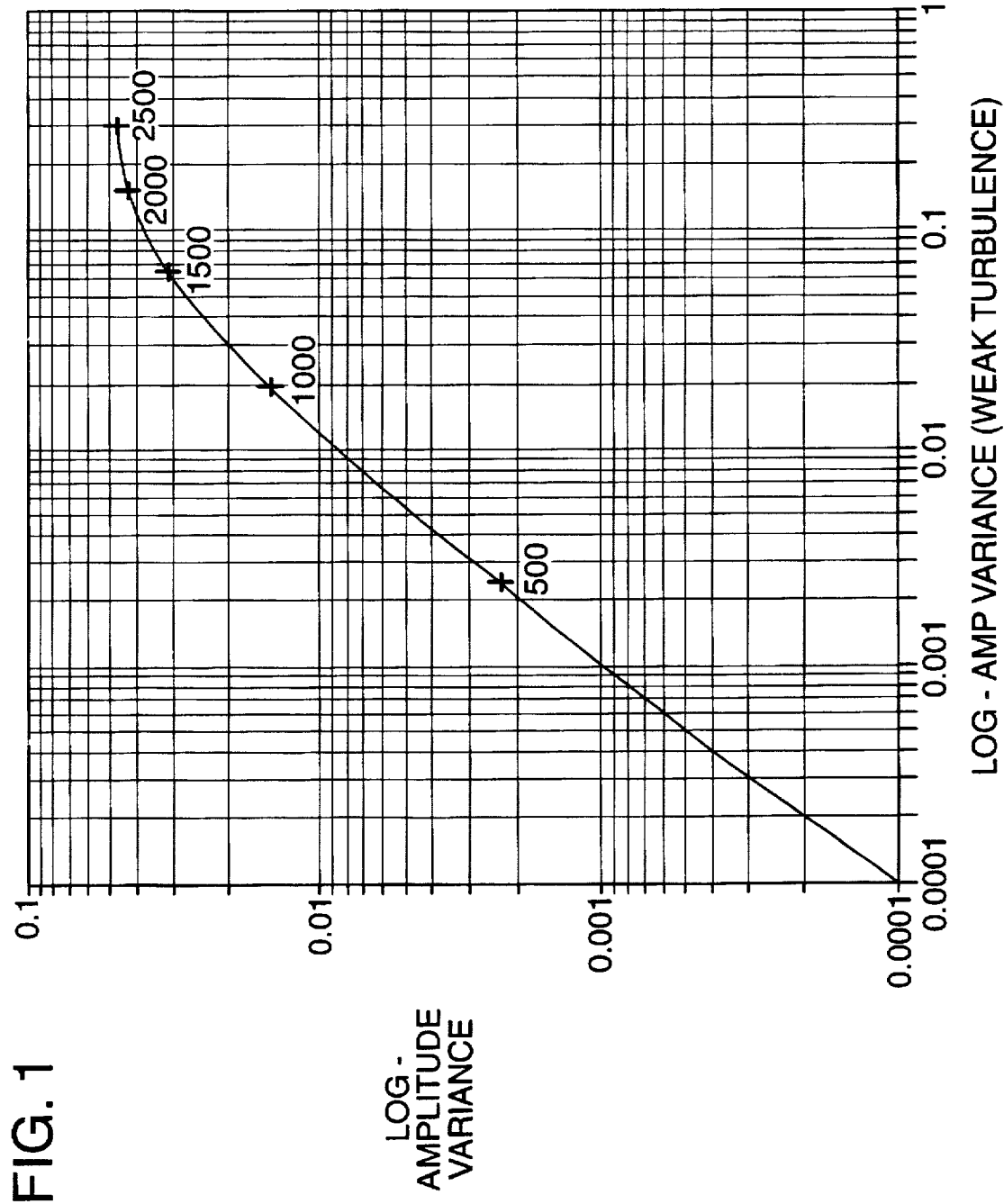
FIG. 1 graphically illustrates the log-amplitude variances $\sigma_x^2$ versus the weak scattering log-amplitude variance $\sigma_D^2$ for various path lengths from 0.5 kilometers to 2.5 kilometers where D is equal to 0.15 meters, and $C_n^2$ equals $10^{-12}$ $m^{-\frac{2}{3}}$.

The log-amplitude variances $\sigma_x^2$ as a function of the weak scattering predicted variance $\sigma_D^2$ (neglecting the exponential term in Equation (3)) for finite aperture are plotted in FIG. 1 for D=0.15 meters, $C_n^2=10^{-12}$ $m^{-\frac{2}{3}}$, and for various path lengths from 0.5 kilometer to 2.5 kilometer. For different $C_n^2$ values, the results are extremely close to that of FIG. 1, therefore, an empirical relationship between $\sigma_x^2$ and $\sigma_D^2$ can be expressed as:

$$\sigma_x^2=0.27*\sigma_D^2*exp(-48*\sigma_D^2)+0.047*(1-exp(-15.53*\sigma_D^2)), \quad (6)$$

or $$\sigma_D^2=0.021*(exp(40.5*\sigma_x^2)-1)+0.15*\sigma_x^2/(1-\sigma_x^2/0.47). \quad (7)$$

The atmospheric turbulence refractive structure constant can then be obtained as:

$$C_n^2(m^{-\frac{2}{3}})=4.48\,\sigma_D^2\,D^{7/3}L^{-3}. \quad (8)$$

The received scintillometer signal is processed using these formulas to correct the measured log-amplitude variance to obtain the refractive turbulence even in the saturation regime. The saturation regime or region may be considered to be the atmospheric condition that exists when $\sigma_T^2$ is greater than 0.3. The saturation regions is distinguished from the first order region, which is that region where $\sigma_T^2$ is equal to or less than 0.3. For equal transmitter and receiver apertures of 0.15 meters, the system is able to measure the path-averaged refractive turbulence up to 2.5 kilometers (for $C_n^2=10^{-12}$ $m^{-\frac{2}{3}}$).

Figure 2:
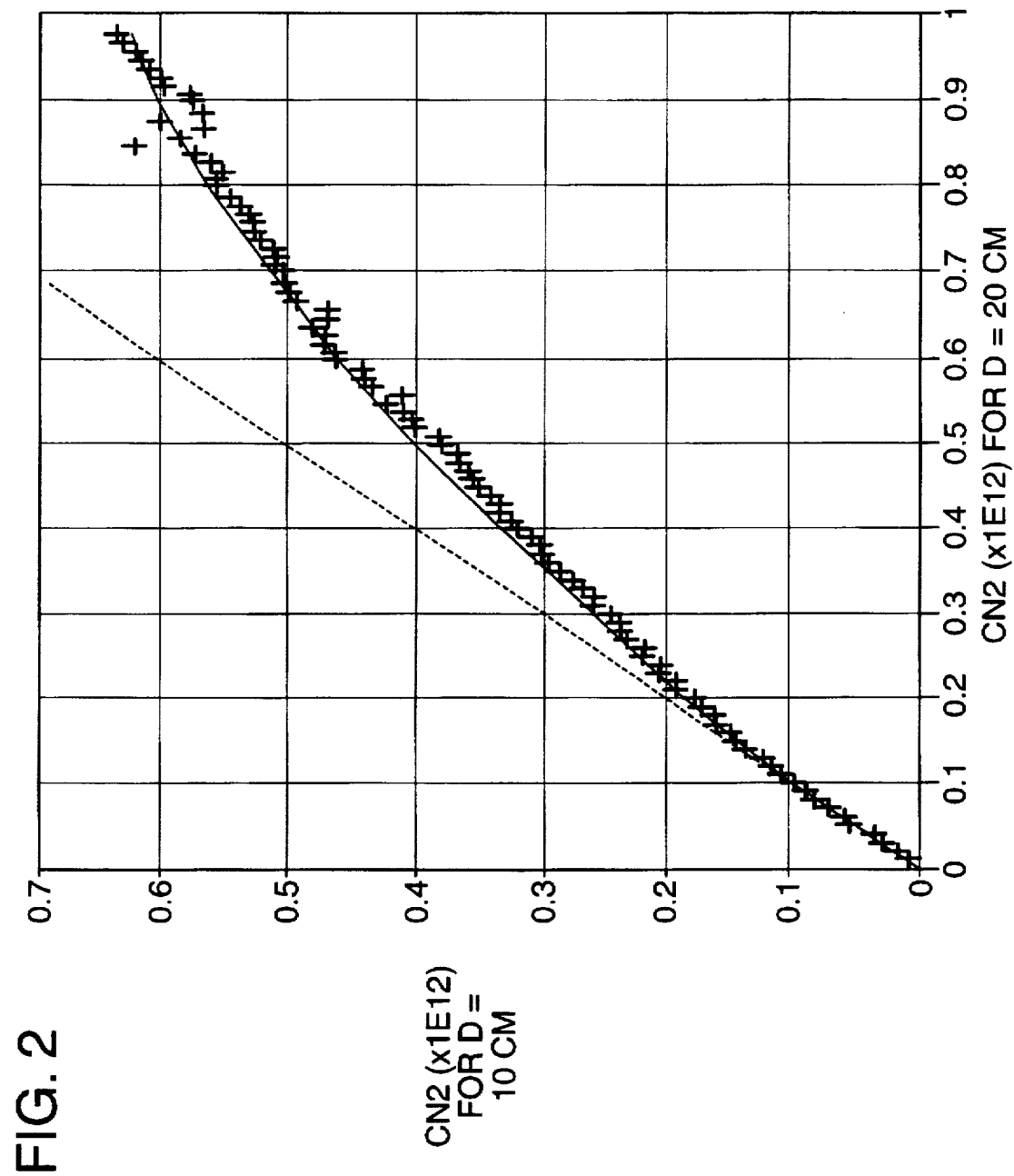
FIG. 2 is a comparison of refractive turbulence indices $C_n^2$ obtained by the ten centimeter and twenty centimeter aperture scintillometers. The solid curve and dashed line are respectively the theoretical predictions with and without correction for saturation according to Equations (1)–(3), while experimental results are indicated by +'s.

FIG. 2 represents a comparison of refractive turbulence indices $C_n^2$ obtained by 10 cm and 20 cm aperture prior art scintillometers. The solid curve is the theoretical prediction. The +'s are the experimental results. FIG. 2 shows the comparison of the field measured $C_n^2$ of two different sets of equal transmitter and receiver apertures along a 1012 meter path. Saturation effect has been observed from the results of the smaller aperture (D=10 cm) system, which is indicated by the dashed line, when it compared to the results of larger aperture (D=20 cm) system. Theoretical results for these parameters are shown as the solid curve in FIG. 2. The calculated results give excellent agreement with the experimental results (indicated by +'s).

It is extremely difficult if not impossible to implement Equations (7) and (8) using analog circuitry. According to the present invention, a digital signal processing unit has been designed to implement the corrections (Equations (7) and (8)) to measure path integrated turbulence intensities in real time.

Figure 3:
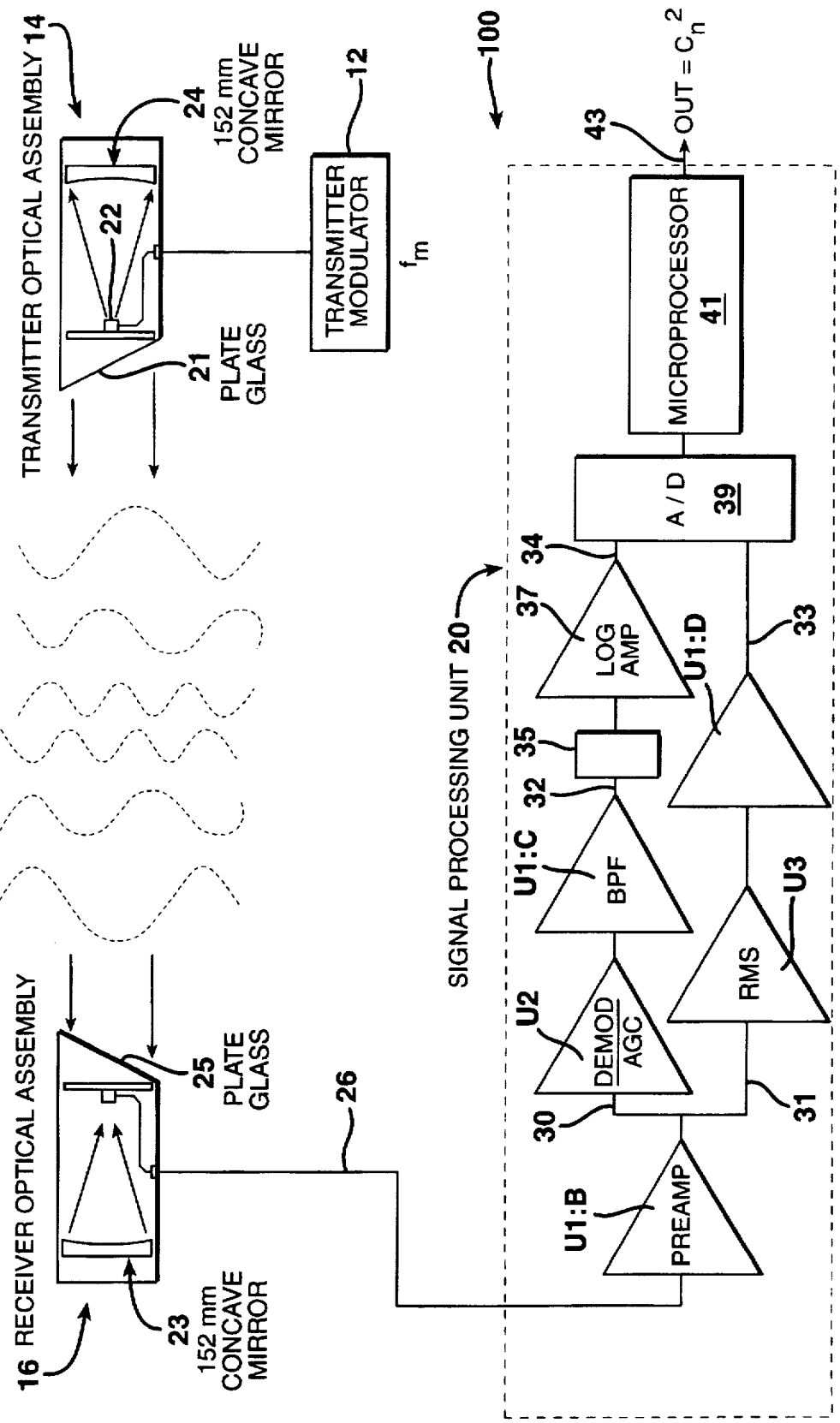
FIG. 3 is a block diagram of an extended range optical scintillometer with interruption protection for measuring atmospheric refractive turbulence.

FIG. 3 is a block diagram of an extended range optical scintillometer 100 with interruption protection that provides an output corrected for atmospheric refractive turbulence. The extended range optical scintillometer 100 is comprised of: an LED transmitter modulator 12, a transmitter optical assembly 14, a receiver optical assembly 16, a photodiode 18, including a preamplifier for the photodiode 18, and a signal processing unit 20.

Transmitter Modulator 12

To minimize the effect of the ambient light, the transmitter LED 22 is modulated at a frequency $f_m$ which is generated by the transmitter modulator 12. The modulation frequency should be higher than that of the scintillation signal. In normal atmospheric conditions, the scintillation frequency is below a few hundred Hertz. Therefore, a modulation frequency of around 10 kHz is appropriate.

Figure 4:
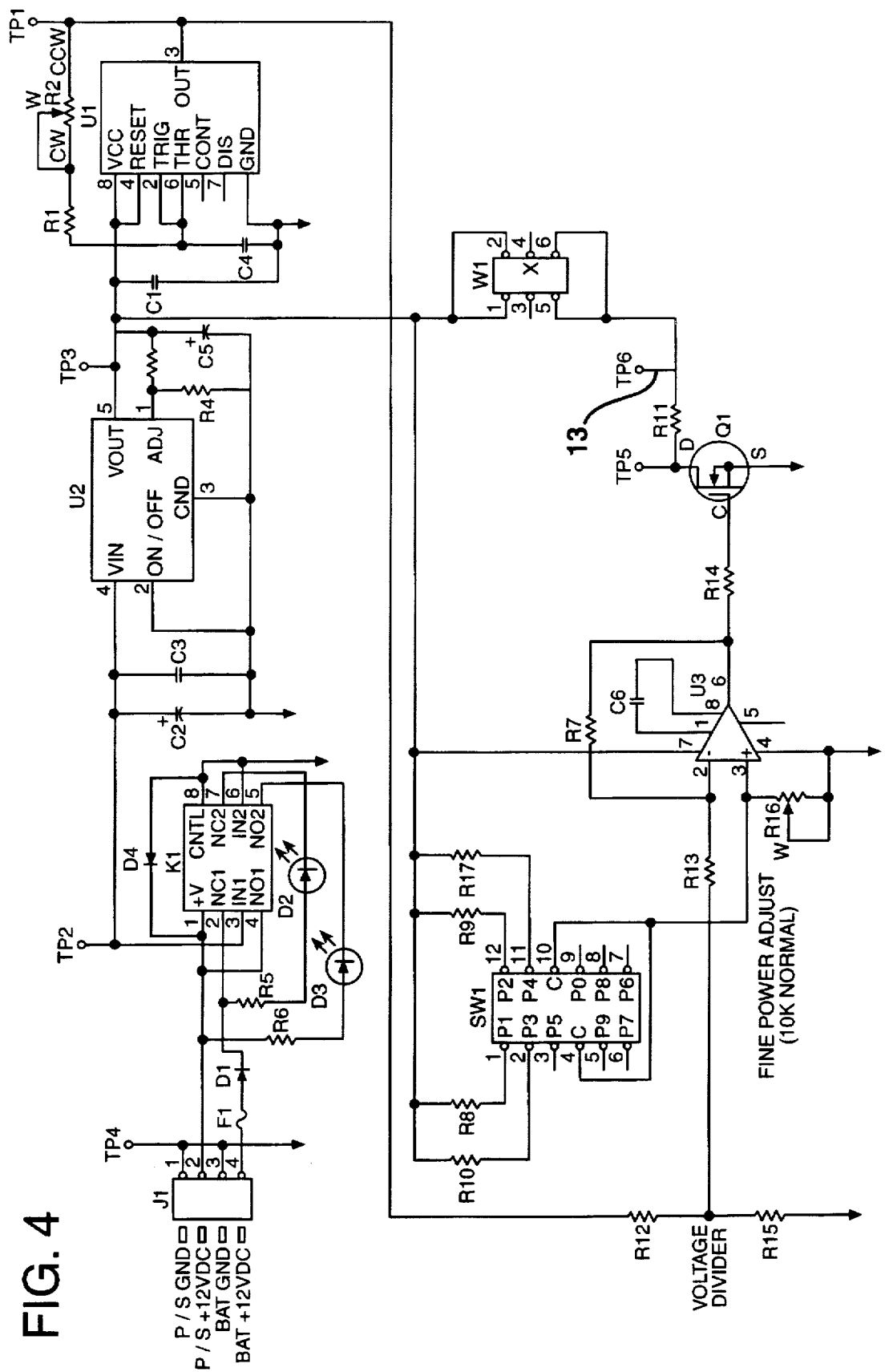
FIG. 4 is a schematic diagram of the transmitter shown in FIG. 3.

FIG. 4 is a circuit diagram of the transmitter modulator 12, which is designed for use with both AC and DC power. The suggested component descriptions, values, and corresponding drawing reference designations are set forth in Table 1. Relay K1 controls the automatic selection of AC or DC power. When DC power (only) is available, the red LED D2 illuminates. When AC or AC and DC power is available the green LED D3 illuminates. The voltage regulator U2 provides a steady 8 volts power for the rest of the circuits. Oscillator U1 provides a 10 kHz square wave. It is buffered by amplifier U3 to provide a modulation signal for transistor Q1 to drive the transmitter LED 22 by the output on line 13. Switch 10 provides the selection of four different power levels of the transmitter LED 22. Output power level is selected in proportion to the path length.

Transmitter Optical Assembly 14

A 152 millimeter (6 inch) concave mirror 24 with a focal length of 300 millimeters, shown in FIG. 3, is used to collimate the infrared light emitted from the infrared LED (light-emitting-diode) 22. A plate glass pane 21 is used to hold the LED 22 at the focal point of the mirror 24, and to seal the unit from dust and the like.

Unlike a laser, an infrared LED is a partially coherent light source. Only through the use of a partially coherent finite aperture system, such as that described herein, can the linear range of the system be extended beyond one kilometer while still avoiding saturation.

Receiver Optical Assembly 16 and Photodiode and Preamplifier 18

A 152 millimeter (6 inch) concave mirror 23 with a focal length of 300 millimeters is used to collect the infrared light emitted from the transmitter 14. A plate glass panel 25 is used to hold the photodiode 18 at the focal point of the mirror 23, and to seal the unit from dust and the like. The photodiode 18 is mounted on a miniaturized printed circuit board with a preamplifier to amplify the receiving signal for data processing.

Signal Processing Unit 20

Figure 5A:
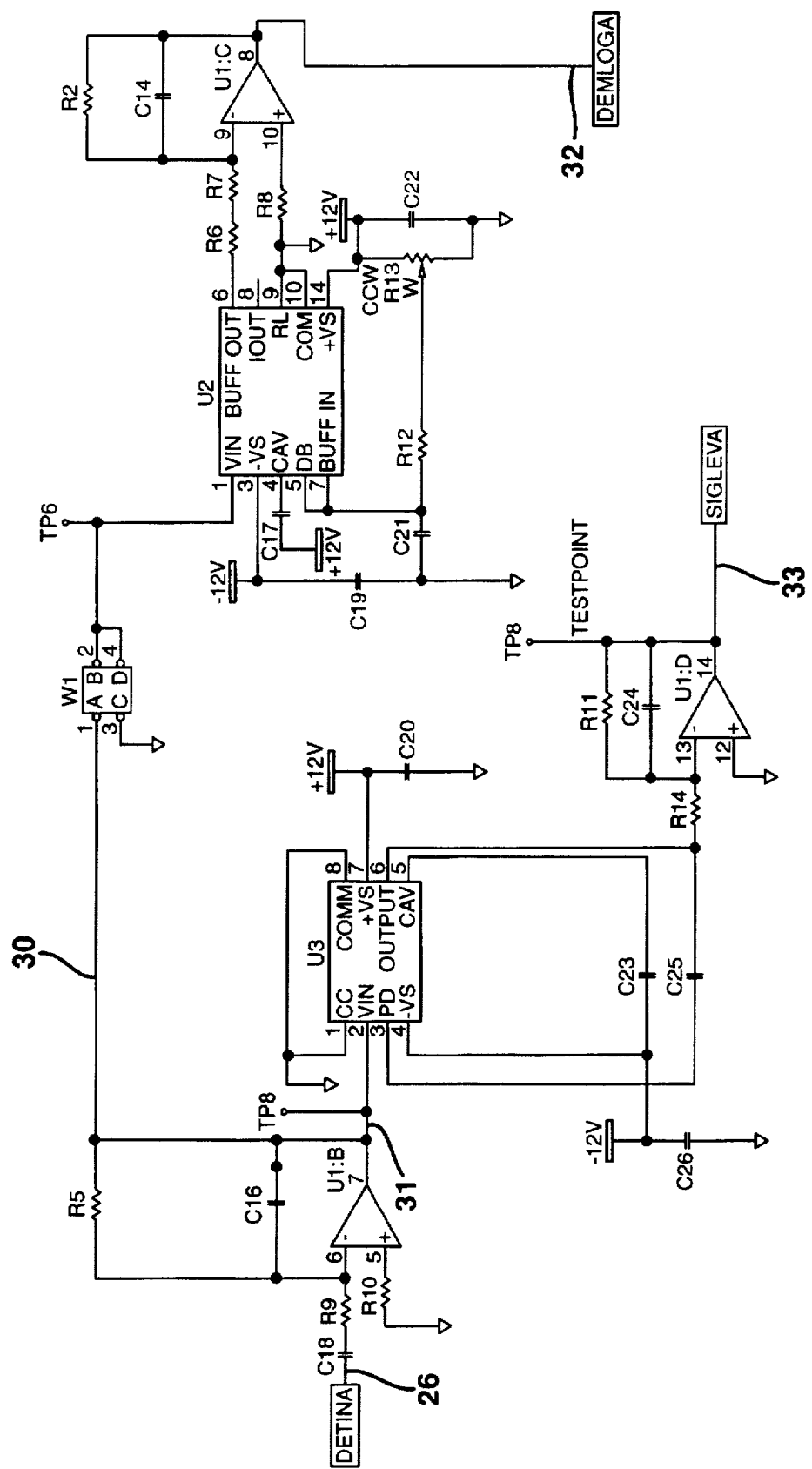
FIG. 5A is a schematic diagram of the analog section of the signal processor shown in FIG. 3.
Figure 5B:
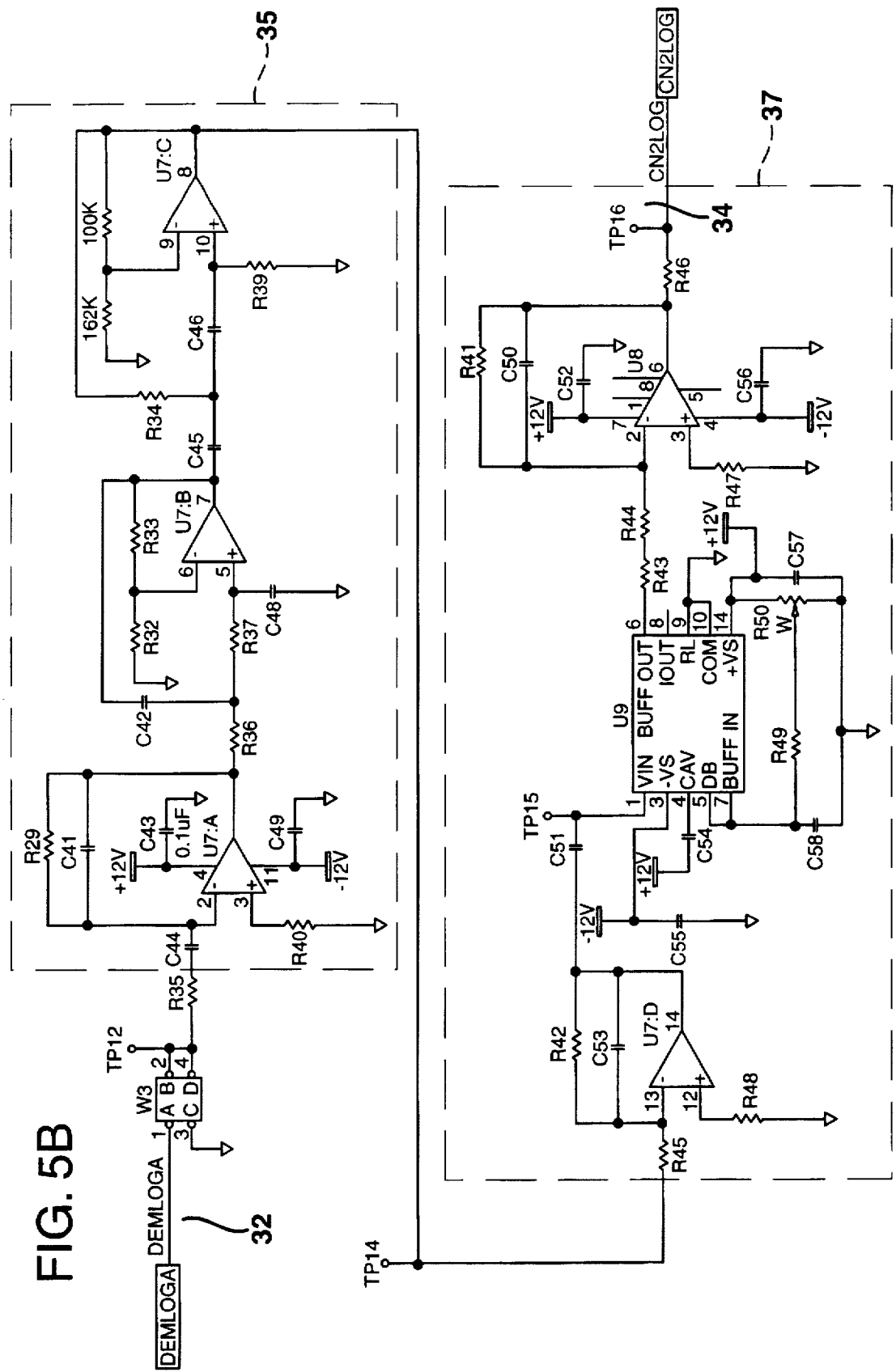
FIG. 5B is a schematic diagram of the remaining part of the analog section of the signal processor shown in FIG. 3.
Figure 6A:
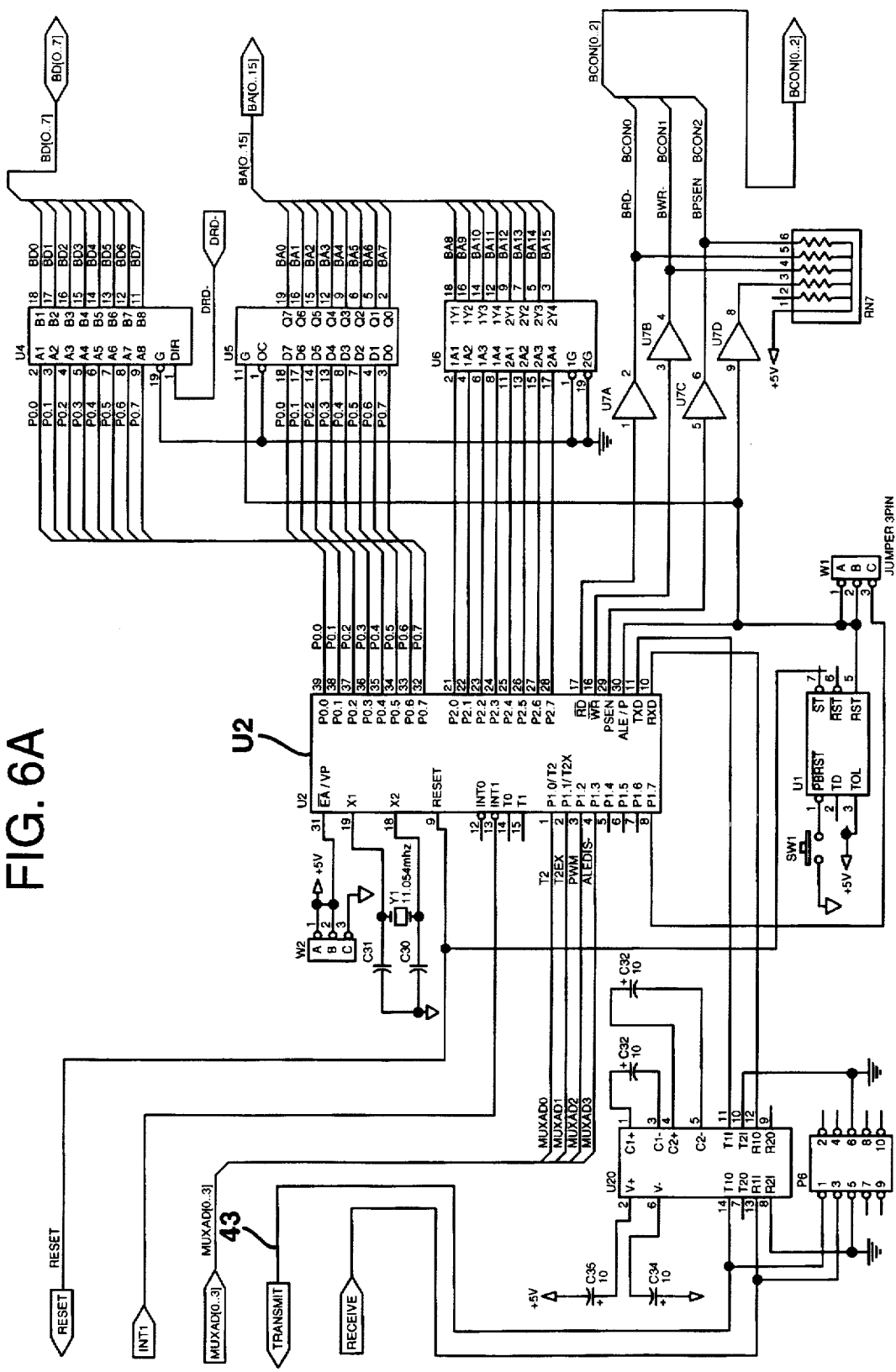
FIG. 6A is the schematic diagram of part of the digital section of the signal processor shown in FIG. 3.
Figure 6B:
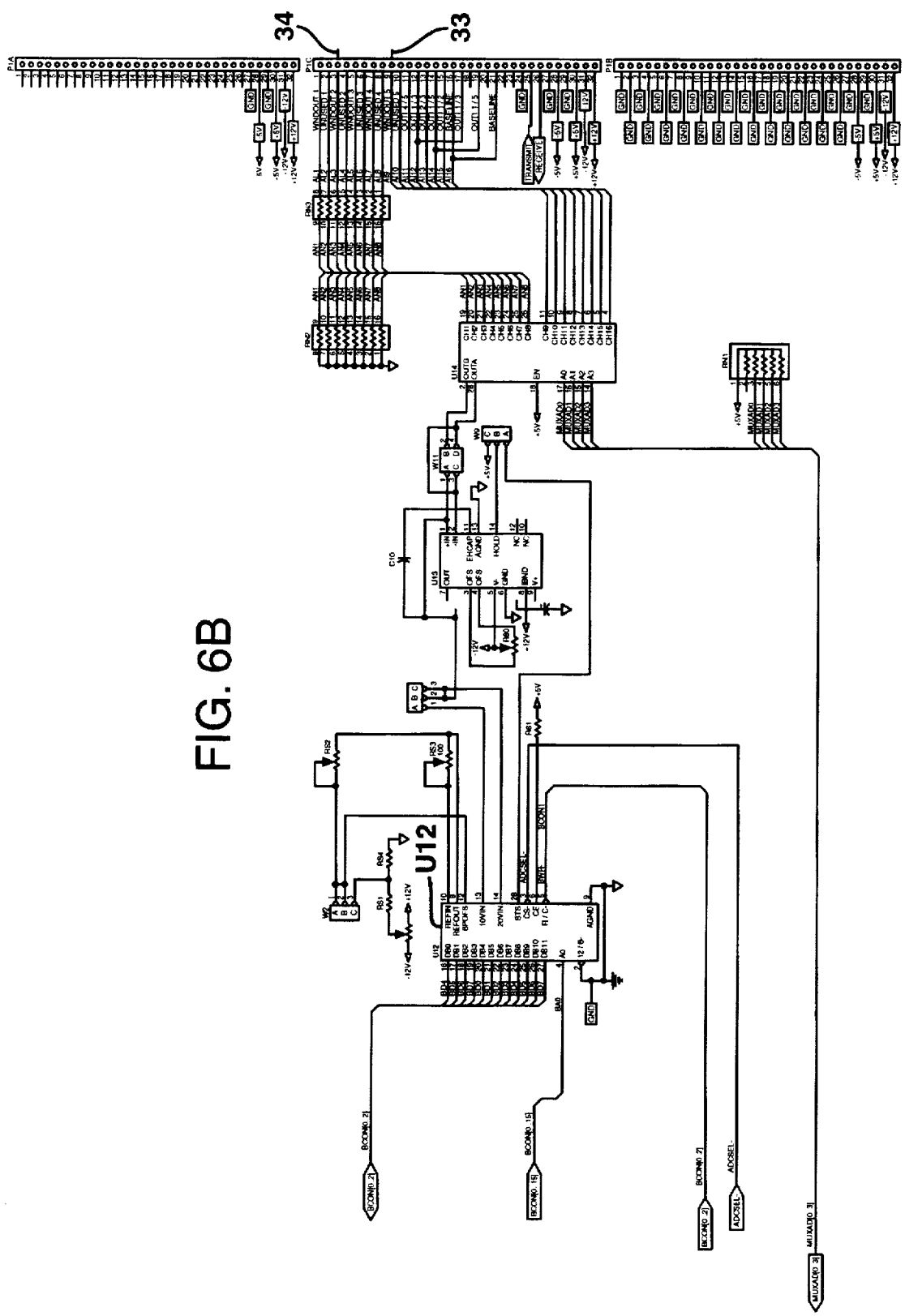
FIG. 6B is a schematic diagram of an additional part of the digital section of the signal processor shown in FIG. 3.
Figure 6C:
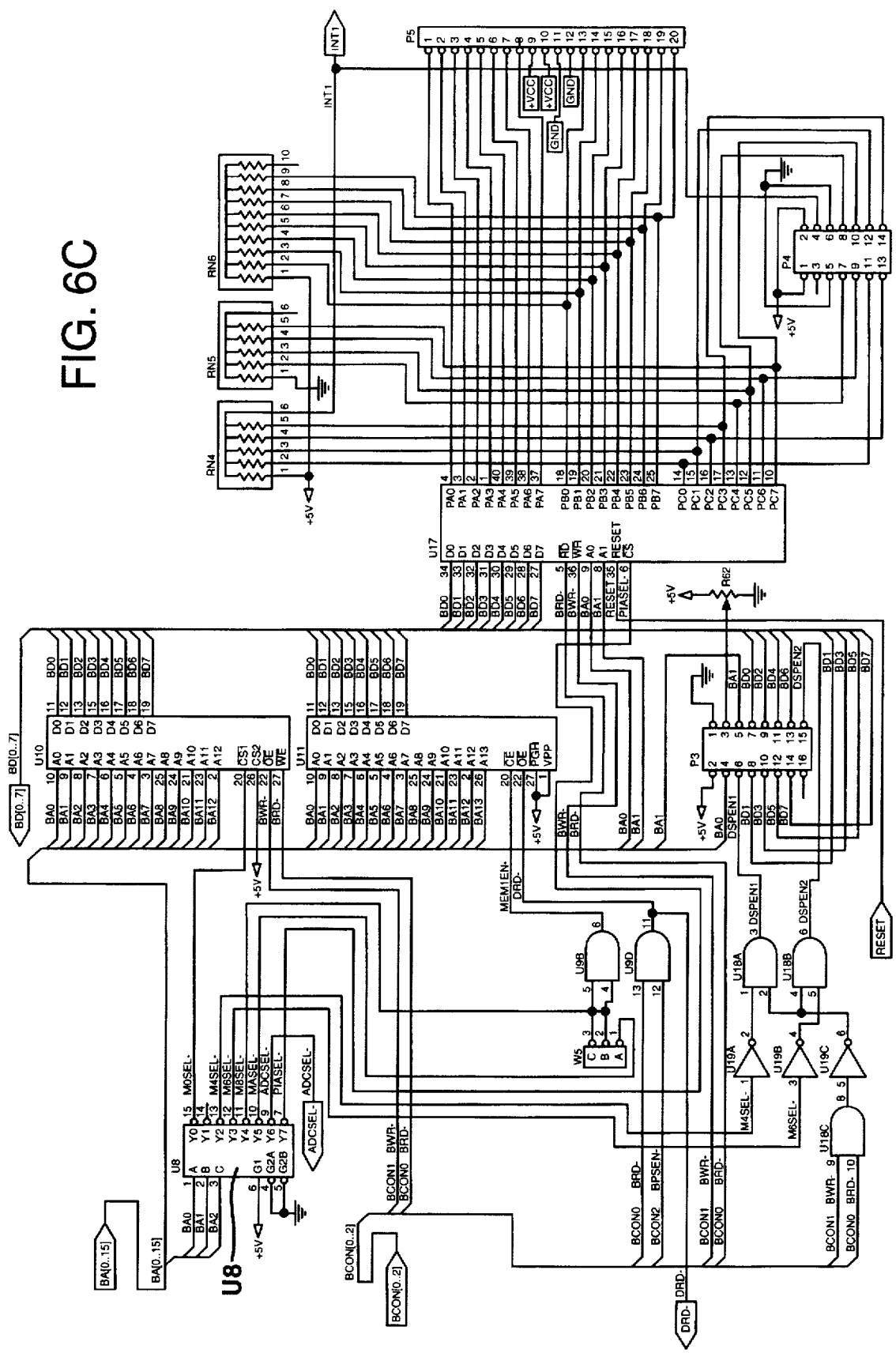
FIG. 6C is a schematic diagram of the remaining part of the digital section of the signal processor shown in FIG. 3.
Figure 7:
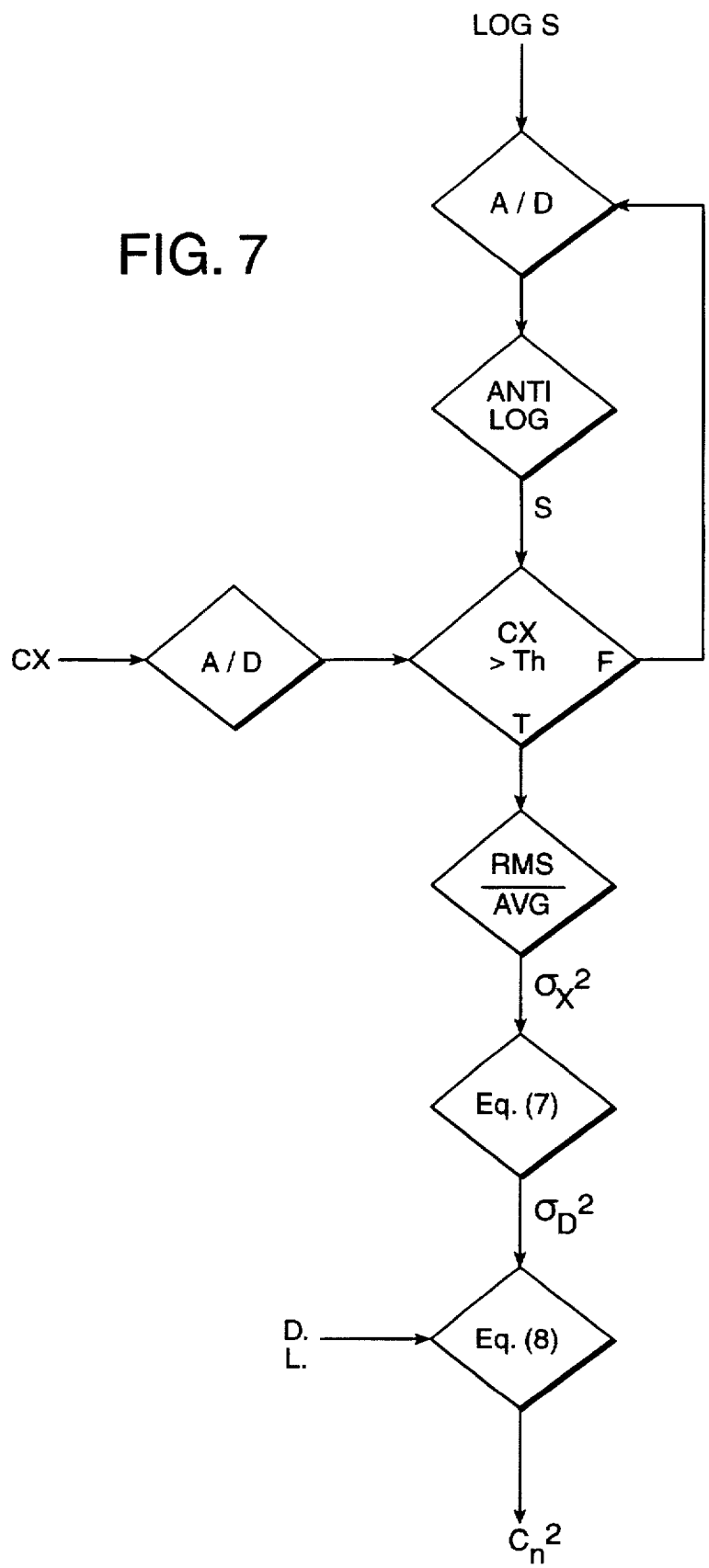
FIG. 7 is a flow diagram illustrating the selective testing of data according to the method of the invention.

The signal processing unit is comprised of an analog section and a digital section. The analog section is shown in FIGS. 5A and 5B. The suggested component descriptions, values, and corresponding drawing reference designations for components shown in FIGS. 5A and 5B are set forth in Table 2. The digital microprocessor section is shown in FIGS. 6A–6C. The suggested component descriptions, values, and corresponding drawing reference designations for components shown in FIGS. 6A, 6B, and 6C are set forth in Table 3. A flow chart of the algorithm software in the digital microprocessor is shown in FIG. 7.

As shown in FIG. 5A, the received analog signal from the receiver 16 enters the signal processor 20 on line 26 and passes through a buffer amplifier U1:B to drive two parallel stages. The signal on line 30 to the first stage is demodulated and normalized by an automatic-gain-control (AGC) logic circuit U2. This ensures that any unnecessary contamination caused by LED aging, dust or dew on the glass plates, and fog or haze of the atmosphere that changes the receiving optical strength will not effect the measurement. The signal from the AGC circuit U2 then passes through a buffer amplifier circuit U1:C. The output on line 32 is then subjected to further signal processing. The signal on line 31 to the other stage passes through a Root-Mean-Square (RMS) circuit U3 and a buffer amplifier circuit U1:D to obtain the signal level of the modulated signal CX on line 33 for further processing.

In FIG. 5B, the signal on line 32 then passes through a band-pass-filter 35 (BPF) that includes IC chips U7:A, U7:B, and U7:C to clean up the signal. The purpose of the BPF 35 is to eliminate background noise outside the band of interest which is around 1 to 400 Hz. The signal then passes through a logarithmic amplifier 37 that is comprised of IC chips U9 and U8 to obtain Log(S) on line 34 for further signal processing.

The analog-to-digital (A/D) converter section 39 and microprocessor section 41 of the signal processor 20, indicated in FIG. 3, are shown schematically in FIGS. 6A to 6C.

As shown in FIG. 6A, an 8-bit microcontroller U2 is connected to a "watchdog" timer and reset generator U1, a data bus transceiver U4, two address latch/bus drivers U5 and U6, and a RS232 level shifter U20. As shown in FIG. 6B, a 12-bit bipolar analog-to-digital converter U12 is connected to a sample and hold stage U13 and to a 16-channel single-ended analog multiplexer (MUX) U14. FIG. 6C schematically shows an address bank decoder U8 that is used to select a 16k×8 static RAM U10, a 16k×8 EPROM U11, the A/D converter U12, or a parallel interface adapter U17 which connects to a hex keypad and LCD display module.

The signals on lines 33 and 34 are digitized by the A/D convertor section 39. The digitized data is then stored in the memory section of the microprocessor 41 for algorithm implementation.

A flow chart of the algorithm is shown in FIG. 7. The digitized signal Log(S) on line 34 is passed through an anti-log operation to convert the logarithmic signal to a linear signal S. The analog multiplexer U14 first selects the CX channel and the analog-to-digital conversion IC chip U12 digitizes the CX signal. The digitized signal CX from line 32 passes through the microcontroller U2 which performs the function of a comparator. If the signal is less than a preset threshold level Th, the data is thrown away and the system waits for the next data. If CX is greater than threshold level Th, the data S passes through a root-mean-square (RMS) and average (AVG) operation performed by the microcontroller U2 to obtain $\sigma_x^2$. The $\sigma_x^2$ can then be converted to $\sigma_D^2$ through Equation (7). The final output of the scintillometer is a standard RS232 interface, shown in FIG. 6A. With input parameter of optics diameter D and path length L, the path-averaged atmospheric refractive turbulence structure constant $C_n^2$ can be obtained from Equation (8) and appears at the output of the RS 232 transceiver U20 on line 43.

A microprocessor controller with key pad and LCD display coupled to the transmit and receive ports of the RS 232 transceiver U20 can be employed for a user interface. The numerical key-pad is very convenient for changing the parameters and display features of the system. The addition of the digital processing unit greatly enhances the system flexibility in field operation. A major advantage of the RS232 interface is that it can be easily connected to any PC, portable or desk-top computer. Therefore, real time data can easily be stored in the hard disc or floppy disc of the PC. Furthermore, sophisticated graphics and data statistics can be displayed on the CRT screen and/or printers.

An extremely important aspect of the invention is the digitization of the signal prior to comparison with the threshold signal. Because a digital signal is compared with a threshold signal level, invalid signal inputs are excluded from the RMS and AVG circuitry by the comparator. The exclusion of such signals will assure the data quality used to compute the refractive turbulence intensity when there is an interruption of the infrared beam. This system therefore differs from prior systems which employ analog inputs into the RMS and AVG circuitry.

Once the signal is digitized, the signal strength CX is compared with a preset threshold. If CX is lower than the threshold, the data is discarded. This test is critical for the data processing. When the optical path is obstructed by moving vehicles, pedestrians, airplanes, or the like, the data will not be used for processing to protect the quality of the output measurements. An analog system typically needs several minutes to recover from a visually obscuring obstruction in the path. In contrast, the digital system of the present invention depicted and described needs only a few seconds after the interruption for recovery. Therefore, the scintillometer 100 can be installed across a highway, a runway, or a hallway without jeopardizing the performance of the instrument.

In addition, it is extremely difficult if not impossible to implement Equations (7) and (8) through analog means. Therefore the prior analog system cannot be use in the saturation regime and hence its effective path length is limited to one kilometer or less. However, the extend range optical scintillometer 100 of the invention can easily implement Equations (7) and (8) through digital microprocessor 41 and thereby extend the effective path length to 2.5 kilometers.

Because the optical scintillometer 100 according to the invention corrects for refractive turbulence it has numerous commercial and military applications. For example, it can be positioned near the runway of an airport. Since data created by moving objects, such as an aircraft, is excluded from the computation process, the beam can even be transmitted across a runway at which aircraft land and take off. Thus, the system can be utilized to detect and signal the presence of dangerous air turbulence conditions, such as wind shear or jumbo jet generated wake vortex conditions that could be life threatening to the passengers and crew of aircraft in the vicinity.

Unlike a scintillometer that processes analog data, the recovery time for a scintillometer according to the invention is almost immediate. That is, since digitized signals which fail to meet the threshold are immediately recognized as being invalid and are excluded, they are never included in the processing performed by the RMS and AVG converter. Therefore, they do not contaminate or contribute to the degradation of valid signals.

Unlike prior scintillometers which have an effective path length of less than one kilometer, even in the saturation region, the log-amplitude variance $\sigma_D^2$ of a finite transmitter and receiver in weak turbulence regions can be calculated according to Equation (7) using the method and apparatus of the invention. From that, turbulence refractive structure constant $C_n^2$ is calculated from Equation (8). Therefore the present invention measures turbulence intensity even in the non-linear region. This increases the effective path length of a scintillometer according to the present invention from less than one kilometer to about two and a half kilometers.

Undoubtedly, numerous variations and modifications of the invention will become readily apparent to those familiar with scintillometers. Accordingly, the scope of the invention should not be construed as limited to the specific embodiment nor the specific manner of implementation of the method depicted and described.

TABLE 1

| Type | Value | Reference Designators |
|---|---|---|
| 1X4HDR | | J1 |
| 2X3HDR | | W1 |
| CAPELEC | 1000 uF | C2 |
| CAPELEC | 22 uF | C5 |
| CAPNP | 0.01 uF | C1, C3 |
| CAPNP | 0.01 uF | C4 |
| CAPNP | 10 pF | C6 |
| DIODE | 1N5400 | D1 |
| DIODE | 1N4148 | D4 |
| FUSE | 2A SLO-BLO | F1 |
| G2R-DPDT | | K1 |
| IRF520 | MOSFET-N | Q1 |
| LED | RED | D2 |
| LED | GREEN | D3 |
| LM2941CT | | U2 |
| LM301AJ | | U3 |
| LOATXM2.S01 | | STI-1506-322 |
| POT | 20.0K | R16 |
| POT | 1.0K | R2 |
| RES | 6.04K | R1 |
| RES | 13.3K | R10 |
| RES | 1 Ohm 2W, 1% | R11 |
| RES | 10.0K | R12, R15 |
| RES | 5.11K | R13, R7 |
| RES | 1.5K | R14 |
| RES | 12.1K | R17 |
| RES | 5.36K | R3 |
| RES | 1.0K | R4 |
| RES | 1K | R5, R6 |
| RES | 18.2K | R8 |
| RES | 15.8K | R9 |
| SWITCH10 | | SW1 |
| TESTPOINT | | TP1, TP2, TP3, TP4, TP5, TP6 |
| TLC555IP | | U1 |

TABLE 2

| Description | Value | Reference Designators |
|---|---|---|
| Capacitor | 0.0015 uF | C14 |
| Capacitor | 0.001 uF | C17, C21 |
| Capacitor | 0.015 uF | C41, C53 |
| Capacitor | 0.033 uF | C42, C48 |
| Capacitor | 0.1 uF | C11, C12, C19, C20, C22, C26, C43, C49, C52, C55, C56, C57, C58, C8, C9 |
| Capacitor | 0.33 uF | C45, C46 |
| Capacitor | 15 pF | C24 |
| Capacitor | 33 pf | C16 |
| Capacitor | 100 uF | C1, C2, C4, C5 |
| Capacitor | 10 uF | C44, C51, C54 |
| Capacitor | 33 uF | C25 |
| Capacitor | 4.7 uF | C50 |
| Capacitor | 100 uF | C23 |
| Capacitor | 47 uF | C18 |
| | DIN96MRA | P1 |
| | AD536A | U2, U9 |
| | TL074 | U1, U7 |
| | AD736 | U3 |
| | LM101AJ | U8 |
| | TESTPOINT | TP1, TP12, TP14, TP15, TP16, TP2, TP3, TP4, TP5, TP6, TP7, TP8 |
| Connector | 2X2HDR | W1, W3 |
| Resistor | 50K | R13, R50 |
| Resistor | 100K | R31, R33 |
| Resistor | 100k | R5 |
| Resistor | 10K | R11, R14, R45, R48 |
| Resistor | 10k | R9 |
| Resistor | 12.1K | R36, R37 |
| Resistor | 150 | R43, R6 |
| Resistor | 162K | R30, R32 |
| Resistor | 1K | R47, R8 |
| Resistor | 20K | R29, R35, R40, R42 |
| Resistor | 220K | R12, R49 |
| Resistor | 226K | R2, R41 |
| Resistor | 34.8 Ohm | R46 |
| Resistor | 470K | R34, R39 |
| Resistor | 8.2k | R10 |
| Resistor | 6.5K TCR | R44, R7 |

TABLE 3

| Description | Reference | Part |
|---|---|---|
| Capacitor | C18, C20 | .1 uF |
| Capacitor | C30, C31 | 27 pf |
| Capacitor | C32, C33, C34, C35 | 10 uF |
| Connector | P1A, P1B, P1C | DIN J 41612 |
| Connector | P3 | HEADER 8 × 2 |
| Connector | P4 | HEADER 7 × 2 |
| Connector | P5 | HEADER 20 |
| Connector | P6 | HEADER 5 × 2 |
| Resistor | R50, R51 | 100K |
| Resistor | R52, R53, R54 | 100 |
| Resistor | R60 | 10K |
| Resistor Rack | RN1, RN7, R61 | 1K |
| Resistor | R62 | 5K |
| Resistor Rack | RN2, RN3 | R-PACK |
| Resistor Rack | RN4 | 2.2K |
| Resistor Rack | RN5 | 22K |
| Resistor Rack | RN6 | 4.7K |
| Switch | SW1 | SW PUSHBUTTON |
| Watch Big Timer Chip | U1 | DS1232 |
| 8-bit Microcontroller | U2 | 8052 |
| Address & Data Bus Buffer & Latch | U4 | 74LS245 |
| Address & Data Bus Buffer & Latch | U5 | 74LS373 |
| Address & Data Bus Buffer & Latch | U6 | 74LS244 |
| Bus Driver | U7 | 7407 |
| 3 of 8 Selector | U8 | 74LS138 |
| AND Gate | U9, U18 | 74LS08 |
| Static RAM | U10 | 6264 |

TABLE 3-continued

| Description | Reference | Part |
| --- | --- | --- |
| EPROM | U11 | 27128/2764 |
| A/D Converter | U12 | HI-574A |
| Sample + Hold | U13 | HA-5320 |
| Analog Multiplexer | U14 | HI-506A |
| Parallel Interface Adapter | U17 | 8255 |
| Inverter | U19 | 74LS04 |
| RS232 Transceiver | U20 | MAX232 |
| Jumper | W1, W2, W5, W8, W9, W10 | JUMPER 3PIN |
| Jumper | W11 | JUMPER 4PIN |
| Crystal | Y1 | 11.054 mhz |

I claim:

1. A method of determining temporally and spatially averaged atmospheric turbulence comprising:

generating an infrared optical signal, partially collimating said infrared optical signal utilizing an optical collimator, transmitting said collimated optical signal through atmosphere over a distance greater than one kilometer and up to 2.5 kilometers, receiving said transmitted optical signal and focusing said transmitted optical signal onto a photodetector utilizing a focusing device, thereby generating received analog signals, converting said received analog signals to digital form to produce received digital signals, comparing each of said received digital signals with a predetermined digital threshold level to produce data output signals for only those of said received digital signals that are at least as great as said predetermined digital threshold level, and calculating the path averaged log amplitude variance of said data output signals to provide an atmospheric turbulence refractive structure constant.

2. A method according to claim 1 further comprising digitally correcting said data output signals for saturation effect of atmospheric turbulence induced optical scintillation.

3. A method according to claim 1 further comprising collimating said optical signal utilizing an optical collimator no greater than about 0.15 meters in size and focusing said transmitted optical signal utilizing a focusing device no greater than about 0.15 meters in size.

4. A method according to claim 1 further comprising transmitting said collimated optical signals to said photodetector through atmosphere over a distance greater than two kilometers.

5. An optical scintillometer that provides an output corrected for air turbulence comprising:

an optical transmitter assembly including an infrared light source and an optical collimating means, an optical receiver assembly located from said optical transmitter assembly a distance greater than one kilometer up to 2.5 kilometers and including an optical focusing means and an infrared photodetector that produces a received signal, and signal processing means for producing an atmospheric turbulence refractive structure constant compensated for refractive turbulence including analog to digital conversion means for converting said received signal from analog to digitized form, comparator means for comparing said digitized received signal with a predetermined digital threshold level and producing data outputs therefrom only when said digitized received signal is at least as great as said digital threshold level, and root mean square determination and signal averaging means coupled to said comparator means to receive outputs therefrom which are processed to provide said atmospheric turbulence refractive structure constant.

6. An optical scintillometer according to claim 5 further comprising digital saturation effect compensation means for correcting said data outputs for saturation effects due to atmospheric turbulence.

7. An optical scintillometer according to claim 5 further comprising digital saturation effect compensation means for correcting said data outputs for variances from first order log amplitude measurement of scintillation intensity due to refractive turbulence.

8. An optical scintillometer according to claim 5 further comprising digital saturation effect compensation means for correcting said data outputs for variance of refractive turbulence from proportionality to log amplitude of scintillation measurements.

9. An optical scintillometer according to claim 5 further characterized in that said optical collimating means and said optical focusing means are each no greater than about 0.15 meters in size.

10. An optical scintillometer according to claim 5 further characterized in that said optical collimating means and said optical focusing means are both concave mirrors each having a diameter no greater than about 0.25 meters.

11. An optical scintillometer according to claim 5 further characterized in that said optical collimating means and said optical focusing means are both concave mirrors each having a diameter no greater than about 0.15 meters.

12. An optical scintillometer according to claim 11 wherein said optical transmitter assembly and said optical receiver assembly are located from each other a distance of at least two kilometers.

13. In a scintillometer for measuring path averaged atmospheric turbulence intensity along a path between an optical transmitter and an optical receiver providing analog data outputs and employing a signal processor that includes root mean square and averaging circuity to provide an atmospheric turbulence refractive structure constant, the improvement comprising an analog to digital converter that digitizes said analog data outputs from said receiver and digital saturation effect compensation means that corrects said data outputs from said receiver in their digital form for variances from first order log amplitude measurement of scintillation intensity due to refractive turbulence.

14. A scintillometer according to claim 13 further comprising comparator means that compares signals from said receiver in their digital form with a predetermined digital threshold level and provides data outputs to said root mean square and averaging circuitry only in response to signals from said receiver in their digital form that are at least as great as said digital threshold level.

15. A scintillometer according to claim 13 further characterized in that said optical transmitter and optical receiver are each comprised of concave mirrors having a diameter of no greater than about 0.25 meters.

16. A scintillometer according to claim 13 further characterized in that said optical transmitter and optical receiver are each comprised of concave mirrors having a diameter of no greater than about 0.15 meters.

* * * * *